US009228996B2

(12) United States Patent
Peppou et al.

(10) Patent No.: US 9,228,996 B2
(45) Date of Patent: Jan. 5, 2016

(54) METHOD AND DEVICE FOR DETECTING DEVICE COLONIZATION (71) Applicant: Empire Technology Development LLC, Wilmington, DE (US)

(72) Inventors: George Charles Peppou, Redfern (AU); Michael Keoni Manion, Redfern (AU); Benjamin Matthew Austin, Redfern (AU); Benjamin William Millar, Redfern (AU); Benjamin Watson Barens, Redfern (AU)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 14/114,738

(22) PCT Filed: May 31, 2013

(86) PCT No.: PCT/US2013/043626
§ 371 (c)(1),
(2) Date: Oct. 29, 2013

(87) PCT Pub. No.: WO2014/193410
PCT Pub. Date: Dec. 4, 2014

(65) Prior Publication Data
US 2014/0356901 A1 Dec. 4, 2014

(51) Int. Cl.
G01N 33/493 (2006.01)
A61B 5/145 (2006.01)
A61M 25/00 (2006.01)
A61L 29/14 (2006.01)
A61L 29/16 (2006.01)
A61B 5/00 (2006.01)
A61L 31/14 (2006.01)
A61L 31/16 (2006.01)
A61F 2/82 (2013.01)

(52) U.S. Cl.
CPC ............ *G01N 33/493* (2013.01); *A61B 5/6852* (2013.01); *A61L 29/14* (2013.01); *A61L 29/16* (2013.01); *A61L 31/14* (2013.01); *A61L 31/16* (2013.01); *A61M 25/0009* (2013.01); *A61B 5/0059* (2013.01); *A61B 5/412* (2013.01); *A61B 5/4851* (2013.01); *A61F 2/82* (2013.01); *A61L 2300/602* (2013.01); *A61M 25/0017* (2013.01); *A61M 25/0045* (2013.01); *A61M 2025/0056* (2013.01); *A61M 2205/702* (2013.01); *G01N 2800/00* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 3,881,993 A | 5/1975 | Freake et al. | |
| 5,103,817 A | 4/1992 | Reisdorf et al. | |
| 5,645,824 A | 7/1997 | Lim et al. | |
| 5,788,687 A | 8/1998 | Batich et al. | |
| 6,306,422 B1 * | 10/2001 | Batich et al. | 424/423 |
| 6,413,778 B1 | 7/2002 | Carpenter et al. | |
| 6,551,346 B2 | 4/2003 | Crossley | |
| 7,824,180 B2 | 11/2010 | Abolfath et al. | |
| 8,061,292 B2 | 11/2011 | Ahmed et al. | |
| 8,062,234 B2 | 11/2011 | Stickler et al. | |
| 8,425,996 B2 | 4/2013 | Gorski et al. | |
| 2004/0253185 A1 | 12/2004 | Herweck et al. | |
| 2005/0131356 A1 | 6/2005 | Ash et al. | |
| 2005/0197634 A1 | 9/2005 | Raad et al. | |
| 2006/0084127 A1 | 4/2006 | Ericson | |
| 2007/0154621 A1 | 7/2007 | Raad | |
| 2008/0085282 A1 | 4/2008 | Yu et al. | |
| 2009/0305331 A1 | 12/2009 | Ben-Horin et al. | |
| 2010/0010327 A1 | 1/2010 | Merz et al. | |
| 2010/0041753 A1 | 2/2010 | Eldridge | |
| 2010/0150989 A1 | 6/2010 | Hoffman et al. | |
| 2010/0233021 A1 | 9/2010 | Sliwa et al. | |
| 2010/0316643 A1 | 12/2010 | Eckert et al. | |
| 2011/0200655 A1 | 8/2011 | Black et al. | |
| 2011/0274593 A1 | 11/2011 | Gorski et al. | |
| 2012/0150096 A1 | 6/2012 | Li et al. | |
| 2013/0041238 A1 | 2/2013 | Joseph et al. | |
| 2013/0064772 A1 | 3/2013 | Swiss et al. | |

FOREIGN PATENT DOCUMENTS

| | | |
|---|---|---|
| WO | WO0024438 | 5/2000 |
| WO | WO2006/000764 A1 | 1/2006 |

OTHER PUBLICATIONS

PubChem. Methylene blue. Datasheet [online]. NCBI NIH. Create date: Mar. 26, 2005. [retrieved on Mar. 3, 2015]. Copyright NCBI. NLM.NIH. Bethesda, MD. Retrieved from the Internet: <URL: http://pubchem.ncbi.nlm.nih.gov/compound/6099. pp. 1-47. specif. pp. 1, 15 and 16.*

Flemming, H.-C. et al. Sep. 2010. The biofilm matrix. Nature Reviewsl Microbiology 8:623-633. specif. p. 627.*

Peter, C. et al. 2000. Pharmacokinetics and organ distribution of intravenous and oral methylene blue. European Journal of Clinical Pharmacology 56: 247-250. specif. pp. 247-249.*

Matsui, A. et al. 2010. Real-time, near-infrared, fluorescence-guided identification of the ureters using methylene blue. Surgery 148: 78-86. specif. pp. 78 and 82.*

Int'l Search Report and Written Opinion, PCT/US13/043626, mailed Sep. 4, 2013, 8 pages.

(Continued)

Primary Examiner — John S Brusca
Assistant Examiner — Sharon M Papciak
(74) Attorney, Agent, or Firm — The Juhasz Law Firm (57) ABSTRACT Technologies are disclosed for a method and a device for detecting device colonization. Disclosed herein is an indwelling medical device configured to detect a biofilm. The device comprises a substrate configured to contact blood and a detecting material, disposed with the substrate, configured to detect the presence of a biofilm thereon. The detecting material is soluble in blood, removable by kidneys from the blood, and passable to urine by the kidneys for detection in the urine. A method for detecting the growth of a biofilm on an indwelling medical and a method for making an indwelling medical device are also disclosed herein.

28 Claims, 5 Drawing Sheets (56) References Cited

OTHER PUBLICATIONS

Int'l Search Report and Written Opinion, PCT/US13/043552, mailed Aug. 30, 2013, 8 pages.

Int'l Search Report and Written Opinion, PCT/US13/43546, mailed Oct. 24, 2013, 12 pages.

Vichaibun, Virun, Chulavatnatol, V. V. (2003). A New Assay for the Enzymatic Degradation of Polylactic Acid. Science Asia, 297-300.

Das RN, K. Y. (May 2012). Diffusion and birefringence of bioactive dyes in a supramolecular guanosine hydrogel. Chemistry, 6008-6014.

Erbel, R. (2007). Temporary scaffolding of coronary arteries with bioabsorbable magnesium stents: a prospective, non-randomised multicentre trial. Lancet, 1869-1875.

Gillman, P. K. (2010). CNS toxicity involving methylene blue: the exemplar for understanding and predicting drug interactions that precipitate serotonin toxicity. Journal of Psychopharmocology, 429-436.

K.A. Athanasiou, J. S. (2007). The Effects of Porosity on in Vitro Degradation of Polylactic Acid—Polyglycolic Acid Implants Used in Repair of Articular Cartilage. Tissue Engineering, 53-63.

Mulvana H, B. R. (Jul. 2012). Albumin Coated Microbubble Optimization: Custom Fabrication and Comprehensive Characterization. Ultrasound Med. Biol.

Nikolaos A. Peppas, N. K. (1997). Ultrapure poly(vinyl alcohol) hydrogels with mucoadhesive drug delivery characteristics. European Journal of Pharmaceutics and Biopharmaceutics, 51-58.

Ren, J. (2011). Biodegradable Poly (Lactic Acid): Synthesis, Modification, Processing and Applications. Springer.

Oldak, Ewa, Trafny, E. O. (Aug. 2005). Secretion of Proteases by Pseudomonas aeruginosa Biofilms Exposed to Ciprofloxacin. Antimicrobial Agents and Chemotherapy, 3281-3288.

Biofilms: A microbial home, J Indian Soc Periodontol. Apr.-Jun. 2011; 15(2): 111-114.

Efficacy of Bio-Synthesized Silver Nanoparticles Using Acanthophora Spicifera to Encumber Biofilm Formation, P. Kumar et al., Digest Journal of Nanomaterials and Biostructures vol. 7, No. 2, Apr.-Jun. 2012, p. 511-522.

Rinaudo CD et al. (2010) Specific Involvement of Pilus Type 2a in Biofilm Formation in Group B *Streptococcus*. PLoS One 5(2): e9216. doi:10.1371/journal.pone.0009216.

\* cited by examiner

METHOD AND DEVICE FOR DETECTING DEVICE COLONIZATION

CROSS-REFERENCE TO RELATED APPLICATION

The present application is a U.S national stage filing under 35 U.S.C. §371 of International Application No. PCT/US13/43626, filed on May 31, 2013.

TECHNICAL FIELD

The present disclosure is directed toward an indwelling medical device and methods, more specifically toward an indwelling medical device configured to detect a biofilm.

BACKGROUND

Indwelling medical devices in contact with the blood may be prone to biofilm colonization which may lead to sepsis increasing hospital stays, reliance on antibiotics and even fatalities. Biofilm formation on indwelling medical devices in contact with blood is well established. Due to the level of exposure of the region, large amounts of water present, and nutrient availability, biofilm formation is common.

The removal of indwelling medical devices in early stage colonization may allow the risk of infection to be greatly reduced. The detection of biofilm on an indwelling medical device may provide notification that the device should be removed or replaced to mitigate the risk of infection. However, current biofilm detection technology may be limited to complex systems.

Unless otherwise indicated herein, the materials described in this section are not prior art to the claims in this application and are not admitted to be prior art by inclusion in this section.

SUMMARY

Technologies are generally described for a method and a device for detecting device colonization. Disclosed herein is an indwelling medical device configured to detect a biofilm. The device comprises a substrate configured to contact blood and a detecting material, disposed with the substrate, configured to detect the presence of a biofilm thereon. The detecting material is soluble in blood, removable by kidneys from the blood, and passable to urine by the kidneys for detection in the urine. A method for detecting the growth of a biofilm on an indwelling medical and a method for making an indwelling medical device are also disclosed herein.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices, related to method and device for detecting device colonization. Briefly stated, technologies are generally described for a method and a device for detecting device colonization. Disclosed herein is an indwelling medical device configured to detect a biofilm. The device comprises a substrate configured to contact blood and a detecting material, disposed with the substrate, configured to detect the presence of a biofilm thereon. The detecting material is soluble in blood, removable by kidneys from the blood, and passable to urine by the kidneys for detection in the urine. A method for detecting the growth of a biofilm on an indwelling medical and a method for making an indwelling medical device are also disclosed herein.

In describing more fully this disclosure, we make reference to the accompanying drawings, in which illustrative embodiments of the present disclosure are shown. This disclosure may, however, be embodied in a variety of different forms and should not be construed as so limited.

Figure 1:
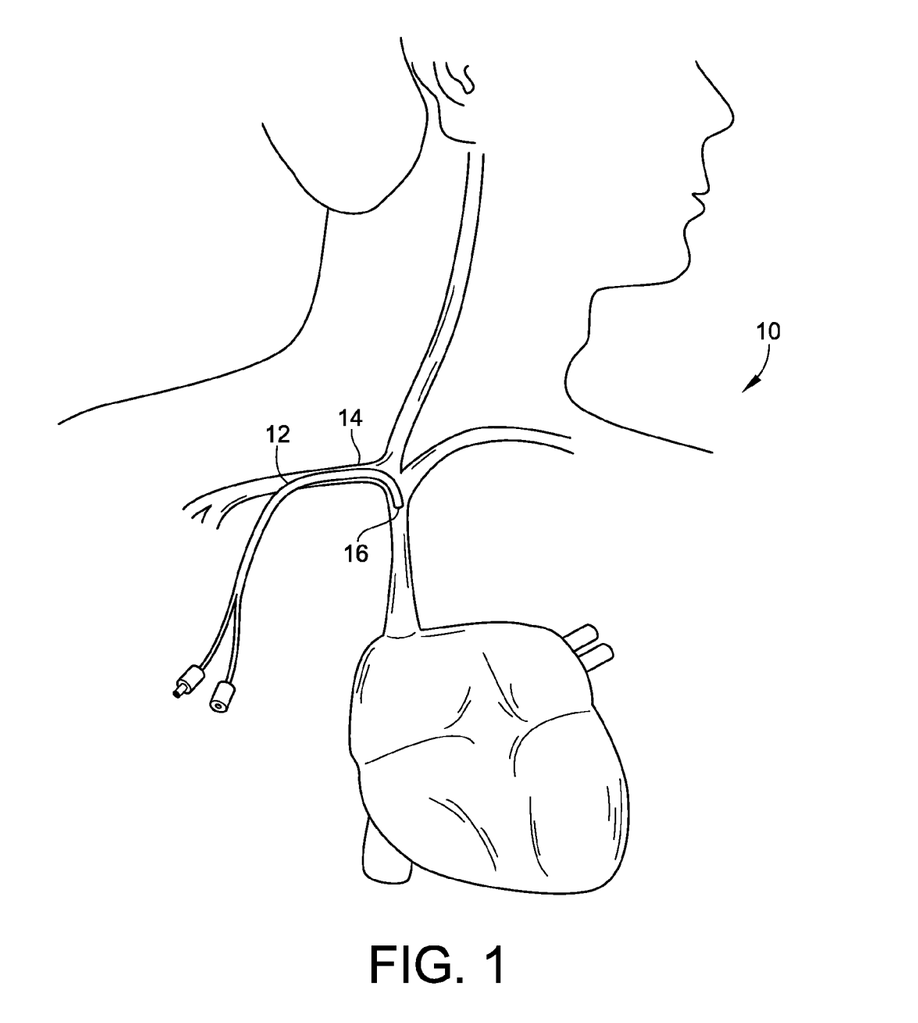
FIG. 1 is a perspective view illustrating an indwelling medical device in use according to this disclosure.

FIG. 1 is a perspective view showing indwelling medical device 10 in use in a patient. In this aspect of the disclosure, the indwelling medical device includes a peripherally inserted central catheter, PICC line 12. However, it is to be understood that any indwelling medical device having a substrate, or portion of a substrate, configured and disposed to contact blood is within the scope of the present disclosure. For example, indwelling medical device 10 may be an intravenous catheter, central line, arterial line, stent, wound drain, or other device having a substrate configured to contact blood. Indwelling medical device 10 shows an example of an indwelling medical device configured for biofilm detection.

PICC line 12 is long, slender, small, flexible tube that is inserted into a peripheral vein 14, typically in the upper arm, and advanced until its tip 16 terminates in a large vein in the chest near the heart to obtain intravenous access. At least a portion of indwelling medical device 10 has a substrate configured and disposed to contact blood. In the aspect of the device shown in FIG. 1, the substrate is in the form of a catheter. For example, a portion of indwelling medical device 10 is configured to detect a biofilm and includes a substrate configured and disposed to contact blood.

Biofilm formation in indwelling devices, such as indwelling medical device 10 illustrated in FIG. 1 is well established. Due to the level of exposure of the region, large amounts of fluids present and nutrient availability the biofilm formation is common. Consequently infection risk is very high, with many patients receiving long-term catheterization receiving an infection.

Degradation kinetics of materials used in indwelling devices in the presence of a biofilm are much studied. Significant research regarding degradation due to a number of microbial species has been well established. For example, where polylactic acid (PLA) is used as the material for the indwelling device, the mechanism of degradation kinetics is known in the art as enzymatic degradation, mediated by a number of proteases, esterases and lipases.

In describing more fully this disclosure, we make reference to the accompanying drawings, in which illustrative embodiments of the present disclosure are shown. This disclosure may, however, be embodied in a variety of different forms and should not be construed as so limited.

Having thus introduced background on indwelling medical devices, we now turn to features that are provided by this disclosure.

Figure 2:
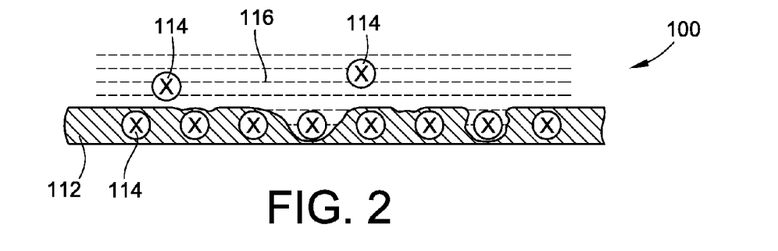
FIG. 2 is a perspective view illustrating an indwelling medical device having a detecting material in a substrate according to this disclosure.

FIG. 2 is a perspective view illustrating an embodiment of an indwelling medical device that may be inserted or implanted into a subject for contacting blood. The blood is shown flowing in FIG. 2 as denoted by dashed lines 116 illustrated in FIG. 2. The medical device includes a substrate 112 including a detecting material 114. Detecting material 114 may be disposed in substrate 112 of indwelling medical device 100 by mixing detecting material 114 with a substrate forming material. For example, polyvinyl chloride (PVC) may be used to make an indwelling medical device such as a catheter. For example, plasticizers used in PVC, a material commonly used to manufacture catheters, have been shown to provide nutrition to the biofilm as the plasticizers diffuse from the polymer matrix.

The indwelling medical device 100 shown in FIG. 2 that may be inserted or implanted into a subject for contacting blood 116 according to an illustrative example of this disclosure is illustratively shown as a catheter in this drawing but can be any insertable or implantable medical device. The catheter may be made from any material that is biomedically friendly to the body. The material from which the catheter is made forms a substrate 112 in this example.

As is known in the art, over time, a biofilm may form on one or more surfaces of materials inserted or implanted into a subject such as the catheter 112 in FIG. 2. The biofilm may form from an aggregation of microorganisms on the surface. These biofilms may digestively feed on the surface where they form; causing that surface of the inserted or implanted material, such as the illustrated catheter, to structurally degrade or otherwise erode. This is shown in FIG. 2 by the recessed portion of the catheter 112.

As also shown in FIG. 2, the substrate 112 holds a dye 114 also denoted in FIG. 2 with the letter X. There are other ways in which the substrate 112 may be formed than by use of the structure of the catheter or other medical device as the substrate. In addition, there are other ways in which dye 114 may be incorporated into the substrate structure and other ways in which dye 114 may be released into the blood from the substrate structure in the presence of a biofilm.

Over time, when the digestive erosion of the wall or substrate 112 has become sufficient, dye 114, which is being held by the substrate 112, is allowed to break free from the substrate 112 and released into the blood 116. This is shown in FIG. 2 with the depiction of dye 114 denoted with the letter X. Once in the blood, dye 114 is absorbed by the kidneys and passed out of the body through urine. When dye 114 is detected in the excreted urine, a caregiver may make decisions based upon the presence dye 114. In at least one embodiment, dye 114 is visually detectable in urine. In one example, if the coloring of the urine from dye 114 is seen to be strong or vivid, the caregiver may decide to remove the catheter. If the coloring from the dye in the urine is weak, the caregiver may provide the patient with an antibiotic to fight the infection or take other steps to counteract the growing infection in the body.

Figure 3:
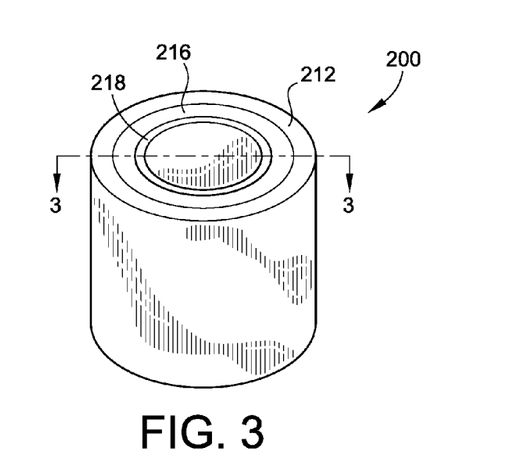
FIG. 3 is a perspective view illustrating an indwelling medical device having a two layer coating on a substrate for detecting device colonization according to this disclosure.
Figure 4:
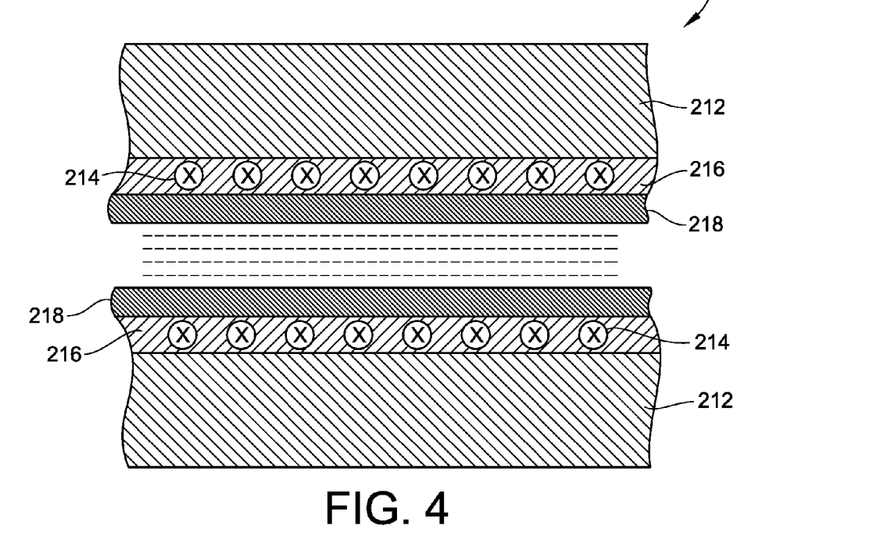
FIG. 4 is a cross-sectional view taken along phantom line A-A of FIG. 3 illustrating an indwelling medical device contacting blood according to this disclosure.

FIGS. 3 and 4 illustrate a portion of an indwelling medical device 200 having a two layer coating on a substrate for detecting device colonization according to this disclosure. FIG. 3 is a perspective view of indwelling medical device 200 and FIG. 4 is a cross-sectional view taken along phantom line A-A of FIG. 3. Indwelling medical device 200 is configured to detect a biofilm and comprises a substrate 212 configured to contact blood. A detecting material 214 is disposed with substrate 212 and is configured to detect the presence of a biofilm thereon. Detecting material 214 is soluble in blood, removable by kidneys (real or artificial kidneys, e.g. dialysis machine) from the blood, and passable to urine, or other fluids removed from the blood, by the kidneys for detection in the urine or removed fluids. As used in this disclosure, the term kidney means a functioning kidney or an artificial kidney, such as a dialysis machine or other artificial system. As used in this disclosure, the term urine means urine produced by a functioning kidney or fluids produced by an artificial kidney. Indwelling medical device 200 further comprises a first layer 216 disposed on substrate 212 of indwelling medical device 200 and first layer 216 comprises detecting material 214. A second layer 218 is disposed on first layer 216. Second layer 218 is degradable in the presence of a sufficient amount of biofilm for the solubilization or release of a detectable amount of detecting material 214 into the blood.

The indwelling medical device may be any implantable or insertable medical device such as intravenous catheters, central and arterial lines, and wound drains. Examples of indwelling medical devices may include angiographic catheters, balloon catheters, biomedical implants, cardiac catheters, cardiac catheter-microphones, central venous catheters, condom catheters, contact lenses DeLee catheters, double-channel catheters, elbowed catheters, electrode catheters, endotracheal tubes, female catheters, fluid-filled catheters, Foley catheters, Gouley catheters, Gruentzig balloon catheters, indwelling catheters, intrauterine devices, mechanical heart valves, needleless connectors, pacemakers, pacing catheters, peritoneal dialysis catheters, prostatic catheters, prosthetic joints, self-retaining catheters, snare catheters, stents, Swan-Ganz catheters, Tenckhoff catheters, toposcopic catheters, two-way catheters, tympanostomy tubes, ureteral catheters, urethral catheter, vascular catheters, voice prostheses, winged catheters. Additionally, reference herein to an indwelling medical device may be referencing only a portion of an indwelling medical device having a substrate configured and disposed to contact blood.

A non-limiting example of an indwelling medical device of the present disclosure may be a catheter, as shown in FIG. 3. As used herein, a "catheter" is a medical device that is inserted into a cavity of the body typically to withdraw or introduce fluid. The catheter typically includes a shaft which may contain one or more lumens. The catheter may be inserted into a subject for introduction of fluids, for removal of fluids, or both. The subject may be a vertebrate subject such as a mammalian subject. Examples of mammalian subjects include a human, a dog, a cat, a horse, etc. Catheters may be soft catheters which are thin and flexible or may be provided in varying levels of stiffness depending on the application. Catheters may be inserted in the body to treat diseases or perform a surgical procedure. A catheter may be an indwelling catheter left inside the body, either temporarily or permanently as a permcath. By modifying the material or adjusting the way catheters are manufactured, catheters may be tailored for a wide range of medical uses including cardiovascular, urological, gastrointestinal, neurovascular, ophthalmic, and other medical applications. Some commonly used catheters include peripheral venous catheters, which may be inserted into a peripheral vein, usually in the hand or arm, for the administration of drugs, fluids, and so on. Some other illustrative examples of catheters have been previously described.

As used herein, a catheter may include various accessory components, subassemblies, or other accessory parts. For instance, a catheter may include molded components, overmolded components, subassemblies, or other accessory components or parts. The catheter may also include connecting fittings such as hubs, extension tubes, and so on. Various catheter tips designs are known. These designs include stepped tips, tapered tips, over-molded tips and split tips for multi-lumen catheters, and so on.

Another non-limiting example of an indwelling medical device is a stent. In an alternative illustrative embodiment, the indwelling medical device is illustratively a stent. A stent is a mold or a device of suitable material used to provide support for structures for holding one or more biomaterials or biostructures in place. These biomaterials and biostructures may include skin, arteries, bodily orifice or cavity, or other biomaterial or biostructure of the body of the subject into which the stent may be placed. Illustrative stents may include biliary, urethral, ureteral, tracheal, coronary, gastrointestinal, esophageal stents, and so on. Stents may be used to treat coronary artery disease, problems in the peripheral vascular system, bile ducts and biliary tree, kidney, urinary tract, trachea, and bronchi. Stents may also be used to treat other medical conditions. The stents may be of any shape or configuration. The stents may include a hollow tubular structure, which may be useful in providing flow or drainage through ureteral, biliary, or other lumens. Stents may be coiled or patterned as a braided or woven open network of fibers, filaments, and so on. Stents may also include an interconnecting open network of articulable or other segments. Stents may have a continuous wall structure or a discontinuous open network wall structure.

As used herein, a stent may include a stent cover which may include a tubular or sheath-like structure adapted to be placed over a stent. The stent cover may include an open mesh of knitted, woven or braided design. The stent may be made of any material useful for providing structure for holding one or more biomaterials or biostructures in place. These materials may include metallic and non-metallic materials. They may also include shape memory materials. Metallic materials may include shape memory alloys such as nickel-titanium alloys. They may also include other metallic materials such as stainless steel, tantalum, nickel-chrome, cobalt-chromium, and so on.

Illustrative materials for use in making the catheter may be a polyvinyl chloride (PVC). Alternatively, materials may illustratively be selected from various grades of biocompatible materials including plasticizers, silicones and latex rubbers. As used herein, the term "biocompatible" means a material that is not substantially toxic to the human body and that does not significantly induce inflammation or other adverse responses in body tissues.

The shaft of a catheter may be made using techniques commonly known in the catheter art. For example, the shaft may be formed by extrusion, such as by a thermoplastic extrusion or a thermoset extrusion as is well known in the catheter art. A coating process such as solvent casting may also be used to form the shaft.

The shaft of a catheter may include one or more dyes or other detecting materials. The shaft of a catheter may also be provided with a coating that may be provided with one or more of dyes or detecting materials.

In FIGS. 3 and 4, the detecting material 214, disposed with substrate 212, is configured to detect the presence of a biofilm thereon. Detecting material 214 may include dyes which may include visible dyes or dyes not visible to the eye. For example, detecting material 214 may be visually detectable in urine and may comprise a dye such as methylene blue, β-carotene, rifampin, Yellow No. 6, tetracycline, Red No. 40, Red No. 3, Blue No. 2, Evan's Blue, Green No. 3, Blue No. 1, indocyanine green, and betanin.

Non-visible dyes may also be used with this disclosure and may include biocompatible fluorescing dyes with dye selection depending on the intended use. In order to view dyes with an emission wave band outside of the visible spectrum of waves, energy must be delivered to the dye to excite the molecules and the resulting emission by the molecules must be collected by specialized equipment sensitive to this non-visible band of waves. Various illustrative methods and devices for delivering energy to dyes with emission outside the visible band of waves and for detecting the wavebands emitted by the dyes in response to excitation are well known.

It will be appreciated that any suitable dye may be used in conjunction with the present disclosure, so long as it is effective for detection directly, such as detection visibly, or indirectly, such as with the assistance of a machine or apparatus or by a test on a fluid specimen containing the dye involving a chemical or other reaction, and is not unduly unsafe for the subject. Combinations of dyes may also be used with this disclosure. Those skilled in the art will recognize that dyes other than those listed above may be used so long as it is effective for detection directly, such as detection visibly, or indirectly, such as with the assistance of a machine or apparatus, or by a test on a fluid specimen containing the dye involving a chemical or other reaction, and is not unduly unsafe for the subject.

In the illustrative example of FIGS. 3 and 4, detecting material 214 is illustratively disposed with substrate 212 and is configured to be released into the blood on the occurrence of an elevated biofilm formation. In the illustrative example, detecting material 214 is disposed in first layer 216. First layer 216, comprising detecting material 214, may be formed in several ways such as using a crystalline dye, inclusion of dye in a hydrogel, or doped into a soluble polymer. The first method may require the device to dipped into a bath of a high concentration solution of solvate dye, the device may then removed and dried to allow the dye to crystallize across the surface before the second polymer is applied. The second method may require the device to first be coated with a hydrogel containing a high dye concentration. Controlled diffusion of bioactive dyes from hydrogel media may be realized using a selected hydrogel, for example guanosine and 8-bromoguanosine hydrogel. A further method of providing the dye is to apply it as a doped soluble polymer such that as the second layer is degraded the first layer 216 is able to dissolve into the blood. In this aspect, Polyvinyl alcohol is one material suited to this application, it is water soluble, able to be doped and has a high level of demonstrated biocompatibility. As the surface coating becomes permeable the polymer and the dye dissolves into the blood.

Second layer 218 is disposed on first layer 216 and may comprise a polymer, mixed polymer, or metal. For example, second layer 218 may comprise a biodegradable material, materials such as starch-based polymers, cellulose-based polymers, PLA (polylactic acid), PLG (poly(lactide-co-glycolide)), and PLGA (poly(lactic-co-glycolic acid)), and/or a protein or albumin. Additionally, second layer 218 may comprise one or more metals such as a thin film of iron or magnesium.

EXAMPLE

A catheter formed of polyvinyl chloride (PVC) and configured to detect a biofilm may be made by coating it in a layer of methylene blue doped polyvinyl alcohol (PVA), to a concentration of greater than 10% weight per volume (w/v) methylene blue. The thickness of PVA layer may be between 10-1000 micron. This layer may be applied using dip coating, spray coating or otherwise. A top coating layer or polylactic acid (PLA) may then be applied in a similar manner on the PVA layer. The thickness of the PLA layer may be between 10-1000 microns.

In an example of indwelling medical device 200, first layer 216 may comprise methylene blue and indwelling medical device 200 may have about 10% biofilm coverage and less than 100 mg of dye may be required across or proximate the device surface. This assumes about 50% removal by the kidneys to provide about a 10 ppm solution in the urine, one that may provide a strong color which may be easily detected by the naked eye.

A portion of the indwelling medical device of the present disclosure may comprise other factors in addition to the detecting material. Substrate 212, first layer 216, and/or second layer 218 may comprise at least one antimicrobial or antifouling agent. This includes, but is not limited to, direct antimicrobial compounds, e.g. methylene blue, silver ions, antibiotics or active enzymes to degrade a biofilm exopolymer matrix. For example, the shaft of a catheter may include one or more factors such as an antimicrobial factor, an antifouling factor, enzyme factors, factors to control pH, factors to insolvate crystals, and so on. The shaft of a catheter may also be provided with a coating that may be provided with one or more of these factors.

Antimicrobial factors may include drugs, chemicals, or other substances that either destroy microbes, prevent their development, or inhibit their pathogenic action. Antimicrobial factors may include antibacterial drugs, antiviral agents, antifungal agents, and antiparasitic drugs.

Antifouling factors which may be released concurrently with the dye include, but are not limited to the follow classes: antibiotics, oxidizing agents (e.g. iodine, peroxide), alcohol, bacteriocins, chelating agents, NaCl, $CaCl_2$, $MgCl_2$, surfactants, urea and/or antimicrobial peptides (AMPs). Furthermore, the surfaces of the devices could be antimicrobial surfaces, which can be accomplished by embedding silver, copper, or the quaternary ammonium compound 3-(Trimethoxysilyl)-propyldimethyloctadecyl ammonium chloride (Si-QAC). Also, the surfaces' antimicrobial nature may be enhanced by modifying a physical factor such as surface smoothness or the hydrophobic nature to prevent adhesion.

Enzyme factors known to disrupt biofilm during growth and maturation may include: cellulase, polysaccharide depolymerase, alginate lyase, disaggregatase, esterases, dispersin B, DNase I. Factors to insolvate crystals may include polyphosphates or other agents known to solvate calcium pyrophosphate crystals.

FIGS. 5-8 illustrate alternative illustrative indwelling medical devices of the present disclosure. It is important to note that only portions of indwelling medical devices with a single surface configured for contacting blood are shown for simplicity only. The indwelling medical device of the present disclosure may be configured to contact blood on several surfaces, may have layers on one or more surfaces, and may be configured to detect the presence of a biofilm on more than one surface.

Figure 5:
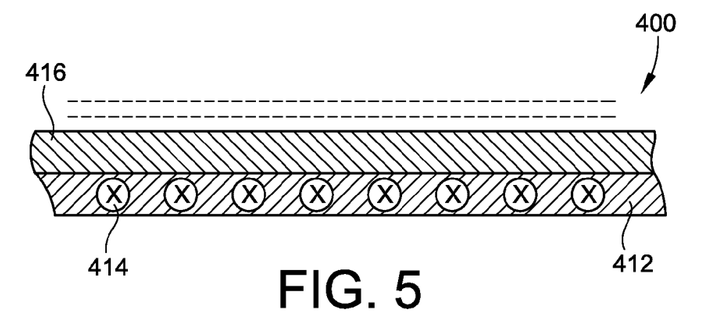
FIG. 5 is a perspective view illustrating an indwelling medical device having a detecting material in a substrate and a coating disposed thereon, according to this disclosure.

FIG. 5 illustrates a portion of an indwelling medical device 400 having a layer or coating 416 and is configured to detect device colonization. Indwelling medical device 400 has detecting material 414 in substrate 412 and a first layer 416 disposed on substrate 412. First layer 416 may be degradable in the presence of a sufficient amount of biofilm for the release of detecting material 414, from substrate 412, into the blood. First layer 416 may comprise a polymer, mixed polymer, or metal. For example, first layer 416 may comprise a biodegradable material.

Substrate 412 has first layer or coating 416 disposed thereon, wherein substrate 412 comprises detecting material 414. First layer or coating 416 may be degradable or otherwise become permeable to detecting material 414 in substrate 412. Indwelling medical device 400, or portion thereof, is configured to detect a biofilm and comprises substrate 412 configured and disposed to contact blood. Detecting material 414 is disposed with substrate 412 and is configured to detect the presence of a biofilm on indwelling medical device 400. Detecting material 414 is soluble in blood, removable by kidneys from the blood, and passable to urine by the kidneys for detection in the urine.

Indwelling medical device 400 comprises a first layer 416 disposed on substrate 412. Substrate 412 comprises detecting material 414. In this illustrative embodiment, second detecting material 414 may be disposed in the substrate 412 by mixing detecting material 414 with a material of composition of indwelling medical device 400 during manufacture. For example, PVC is illustratively used to make catheters and detecting material 414 may be mixed with the PCV during formation.

First layer 416 is degradable in the presence of a sufficient amount of biofilm for the release of detecting material 414, from substrate 412, into the blood. Detecting material 414 may be visually or otherwise detectable in the urine. First layer 416 may comprise a polymer, mixed polymer, or metal. For example, first layer 416 may comprise a biodegradable material, materials such as starch-based polymers, cellulose-based polymers, PLA, PLG, and PLGA, and/or a protein or albumin. Additionally, first layer 416 may comprise one or more metals such as a thin film of iron or magnesium. Substrate 412 and/or first layer 416 may comprise at least one antimicrobial or antifouling agent.

Figure 6:
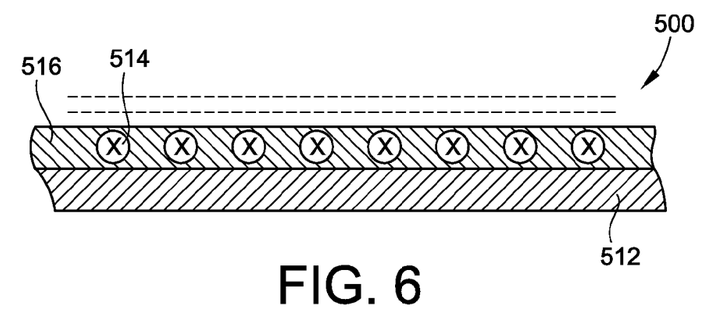
FIG. 6 is a perspective view illustrating an indwelling medical device having a detecting material in a coating on a substrate according to this disclosure.

FIG. 6 illustrates a portion of an indwelling medical device 500 configure to detect device colonization and has a layer or coating 516. Indwelling medical device 500, or portion thereof, is configured to detect a biofilm and comprises substrate 512 configured and disposed to contact blood. Substrate 512 has first layer or coating 516 disposed thereon wherein first layer 516 comprises detecting material 514. First layer 516 may be degradable, or otherwise become permeable to detecting material 514, in the presence of a sufficient amount of biofilm for the release of detecting material 514 therefrom, into the blood. First layer 516 may comprise a polymer, mixed polymer, or metal. For example, first layer 516 may comprise a biodegradable material.

First layer or coating 516 may be degradable or otherwise be altered in the presence of a biofilm for releasing detecting material 514 in blood. Detecting material 514 is disposed with substrate 512 and is configured to detect the presence of a biofilm on indwelling medical device 500. Detecting material 514 is soluble in blood, removable by kidneys from the blood, and passable to urine by the kidneys for detection in the urine.

Indwelling medical device 500 comprises a first layer 516 disposed on substrate 512. First layer 516 comprises detecting material 514 and may be degradable in the presence of a sufficient amount of biofilm for the release of detecting material 514 therefrom, into the blood. Detecting material 514 may become visually detectable in the urine. First layer 516 may comprise a polymer, mixed polymer, or metal. For example, first layer 516 may comprise a biodegradable material, materials such as starch-based polymers, cellulose-based polymers, PLA, PLG, and PLGA, and/or a protein or albumin. Additionally, first layer 516 may comprise one or more metals such as a thin film of iron or magnesium. Substrate 512 and/or first layer 516 may comprise at least one antimicrobial or antifouling agent.

Figure 7:
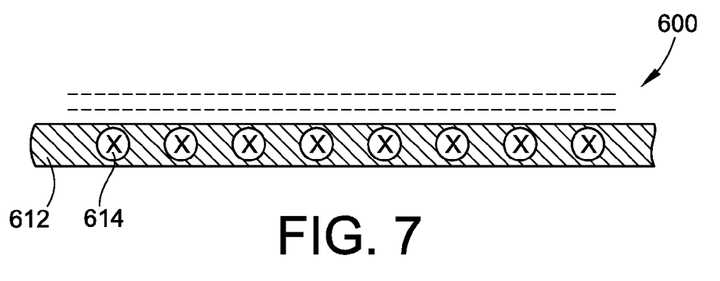
FIG. 7 is a perspective view illustrating an indwelling medical device having a detecting material in a substrate according to this disclosure.

FIG. 7 illustrates a portion of an indwelling medical device 600 configure to detect device colonization. Indwelling medical device 600 comprises substrate 612 configured to contact blood and detecting material 614, disposed with substrate 612, configured to detect the presence of a biofilm thereon. Detecting material 614 is soluble in blood, removable by kidneys from the blood, and passable to urine by the kidneys for detection in the urine.

In this illustrative embodiment, substrate 612 comprises detecting material 614. Detecting material 614 may be disposed in substrate 612 of indwelling medical device 600 by mixing detecting material 614 with PVC illustratively used to make a catheter, for example. For example, plasticizers used in PVC, a material commonly used to manufacture catheters, have been shown to provide nutrition to the biofilm as the plasticizers diffuse from the polymer matrix.

For example, referring back to FIG. 1, PICC line 12, of the indwelling medical device 10, comprises a substrate disposing a detecting material therewith and is configured to detect the presence of a biofilm thereon. The detecting material is soluble in blood, removable by kidneys from the blood, and passable to urine by the kidneys for detection in the urine. At least a portion of indwelling medical device 10 may be configured and disposed to have a single surface or multiple surfaces contact blood. For example, PICC line 12, of the indwelling medical device 10, has an inner and outer surface configured and disposed to contact blood.

Figure 8:
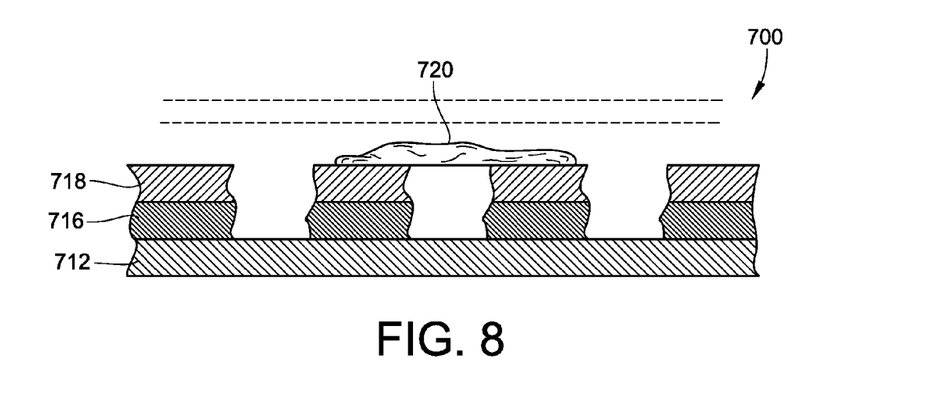
FIG. 8 is a perspective view illustrating an indwelling medical device having a non-degradable portion of a coating according to this disclosure.

FIG. 8 illustrates an aspect of the indwelling medical device 700 of the present disclosure having at least one non-degradable portion of one or more coatings or layers. Indwelling medical device 700 has second layer 718, and optionally first layer 716, both including a first polymer and a second polymer. The first polymer is degraded in the presence of a biofilm and the second polymer is substantially non-degradable in the presence of blood and a biofilm. Indwelling medical device 700 may provide a retaining structure for the biofilm 720, upon the degradation of the first polymer. The second polymer may be most any material that is substantially non-degradable with blood and in the environment of a biofilm, for example, the second polymer may be selected from the group consisting of silicone rubber, polyurethane, and polyethylene.

Indwelling medical device 700 illustrates that rather than utilizing pure polymers, mixes of polymers may be used, one polymer may be degraded in the presence of the biofilm and the second polymer may be substantially non-degradable and may provide structure such that as the first polymer is degraded the overall structure becomes permeable rather than eroding completely. In this aspect of the present disclosure, a readily degraded polymer may be mixed with a structurally supportive polymer. Indwelling medical device 700 may provide a surface for biofilm 720 to remain attached to, thus mitigating or preventing release of the biofilm during device removal.

Indwelling medical device 700 may be made by processing a substantially blood insoluble polymer, such as silicone rubber, polyurethane and polyethylene, mixed with a soluble or degradable polymer or protein. In the presence of a biofilm the surface may be partially degraded, allowing blood to diffuse into the detecting material containing layer and solvate the detecting material. The structural polymer may remain unaffected by the presence of the biofilm, providing a structure for which the biofilm can remain adhered to, preventing any excessive release of free microbes during the device response and removal. The first and second polymers may be incorporated with layer 716, layer 718, or both layers. Additionally, first and second polymers may be incorporated with an indwelling medical device having a single layer, such as layer 416 and 516 of indwelling medical devices 400 and 500, shown in FIGS. 5 and 6.

Figure 9:
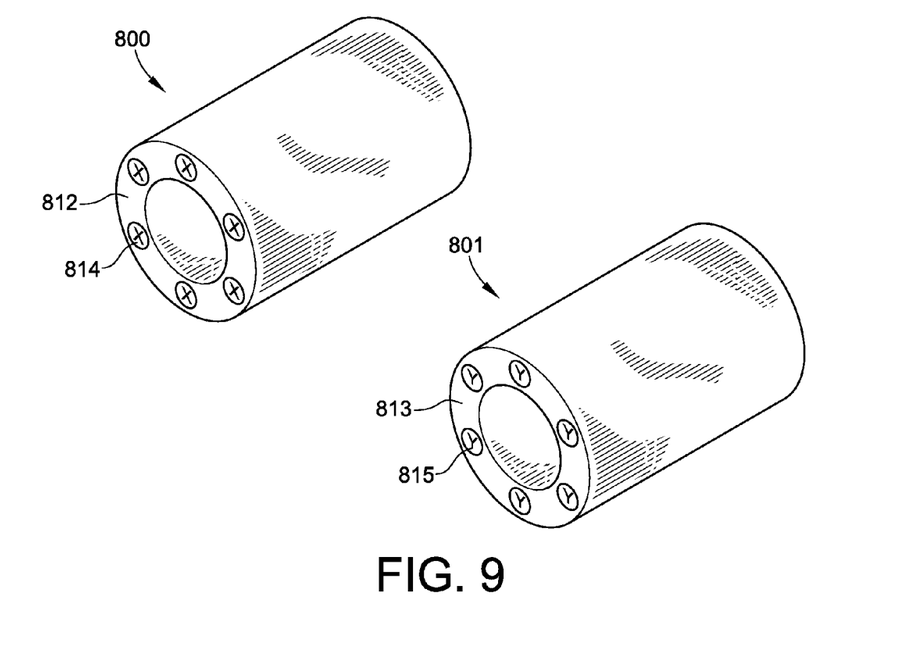
FIG. 9 is a perspective view illustrating a system comprising two indwelling medical devices according to this disclosure.

FIG. 9 illustrates a system including two or more indwelling medical devices according to this disclosure. A system may be configured to independently detect biofilm on two or more indwelling medical devices, 800 and 801. Each indwelling medical device 800 and 801 comprise a substrate, 812 and 813 respectively, configured to contact blood and a detecting material, 814 and 815 respectively, disposed with their substrate configured to detect the presence of a biofilm on their substrate.

Detecting materials 814 and 815 are soluble in blood, removable by kidneys from the blood, and passable to urine by the kidneys for detection in the urine. Each detecting material, 814 designated with "X" and 815 designated with "Y", is associated with a different indwelling medical device, 800 and 801 respectively. Each detecting material, 814 designated with "X" and 815 designated with "Y", is an independently detectable detecting material and the detection of an independently detectable detecting material indicates the indwelling medical device having the biofilm.

As patients often have multiple devices in place at any one time, knowing which of the devices have been colonized may be essential to prevention or mitigation of infection through device removal. To determine which devices have been colonized, each device type may utilize a different dye, such that the color of dye in the urine indicates the device affected. Below is Table 1 demonstrating several example device types which may be in place simultaneously and example dyes and the color they may appear.

TABLE 1

| Device | Dye | Color in urine |
|---|---|---|
| Intravenous cannulae | Indocyanine green | Green |
| Central line | Methylene blue | Blue |
| Wound drains | Rifampicin | Red |

Integration of the system illustrated in FIG. 9 into practice may not require any changes to hospital procedure as the usage of the devices may be unchanged. Higher dependency patients may have a greater risk of acquiring infections during time in the hospital, these patients may generally be treated with urinary catheters in place. Consequently, standard nursing procedures for monitoring urinary output may also monitor for medical device colonization.

Figure 10:
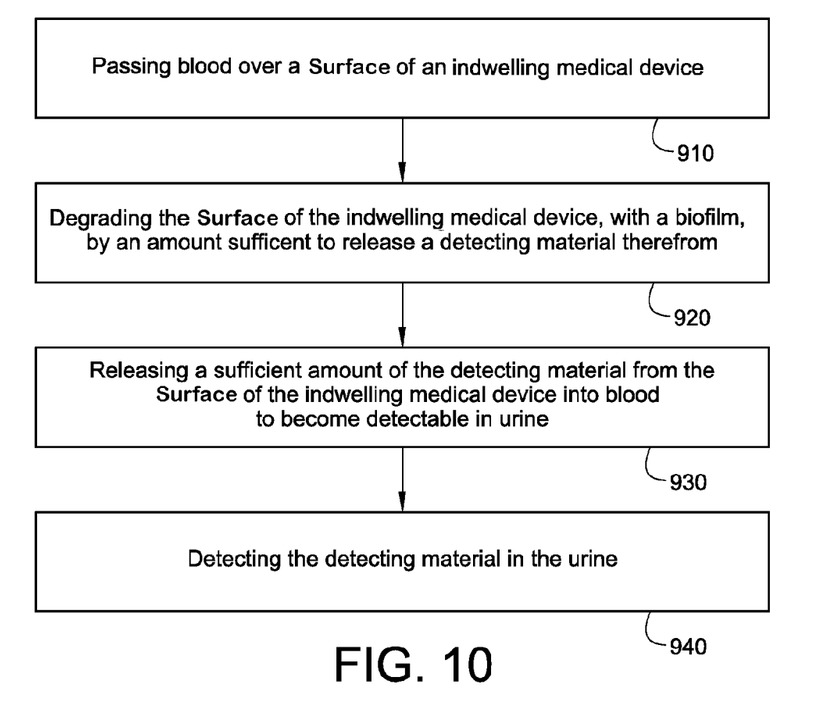
FIG. 10 is a flow diagram illustrating an example process of using a device according to this disclosure.

FIG. 10 illustrates an example process of using a device according to this disclosure. Method 900 for detecting the growth of a biofilm on an indwelling medical device includes passing blood over a surface of the indwelling medical device at step 910. At method step 920, the surface of the indwelling medical device is degraded, with a biofilm, by an amount sufficient to release a detecting material therefrom. Following the degradation of the surface of the indwelling medical device, a sufficient amount of the detecting material is released from the surface of the indwelling medical device into the blood to become detectable in urine at method step 930. Finally, the detecting material is detected in the urine at step 940.

The step of degrading the surface of the indwelling medical device of step 920 may include degrading an outer most surface of the indwelling medical device by a sufficient amount, prior to the step of releasing the detecting material from the surface of the medical device, step 930.

The step of degrading the surface of the indwelling medical device, step 920, may further include exposing a sub-surface of the indwelling medical device to the passing blood and the step of releasing a sufficient amount of the detecting material from the substrate of the indwelling medical device, step 930, may include releasing the detecting material from the sub-surface, upon the step of degrading an outer most surface of the indwelling medical device at step 920.

The step of detecting the detecting material in the urine at step 940 may include visually detecting the detecting material.

Figure 11:
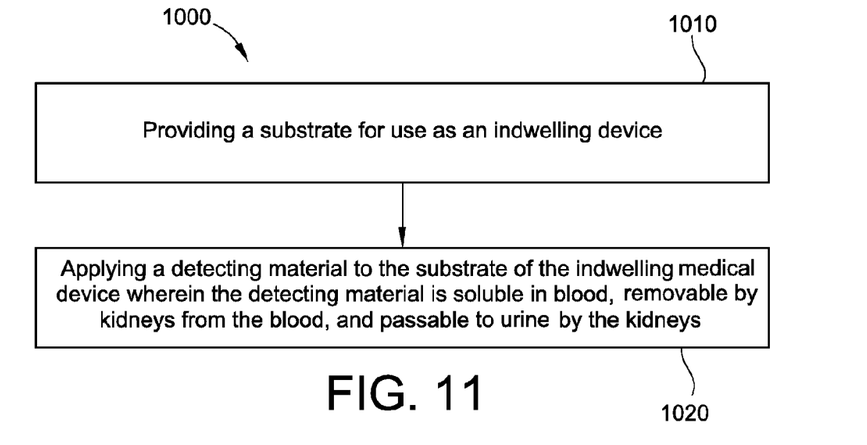
FIG. 11 is a flow diagram illustrating an example process of making a device according to this disclosure, all arranged according to at least some embodiments presented herein.

FIG. 11 illustrates an example process of making a device according to this disclosure. Method 1000 for making an indwelling medical device includes providing a substrate for use as an indwelling device at step 1010. At step 1020, a detecting material is applied to or with the substrate of the indwelling medical device wherein the detecting material is soluble in blood, removable by kidneys from the blood, and passable to urine by the kidneys. For example, step 1020 may include mixing a detecting material with a material of composition of indwelling medical device during manufacture. Illustratively, PVC may be used to make an indwelling medical device and detecting material may be mixed with the PCV during formation of the device.

Method 1000 may further include preparing a bath comprising a crystalline solvate dye. The step of applying a detecting material to the substrate, step 1020, may include coating the substrate of the indwelling medical device with the bath. The coated substrate may then be dried and the dye may then crystallize. A polymer may then be applied onto the crystallized dye.

Method 1000 may further include preparing a hydrogel and dye material and the step of applying a detecting material to the substrate, step 1020, may comprise coating the substrate of the indwelling medical device with the hydrogel and dye material. The hydrogel may be selected from the group consisting of guanosine and 8-bromoguanosine hydrogel. The hydrogel and dye material may be made by doping a first polymer with a dye wherein the first polymer is water soluble. The step of applying a detecting material to the substrate, step 1020, may include coating the substrate of the indwelling medical device with the doped first polymer. Method 1000 may further include applying a second polymer onto the coated substrate, wherein the second polymer is degradable in the presence of a sufficient amount of biofilm for the release of a detectable amount of the dye into the blood. The first polymer may include PVA. The substrate of the indwelling medical device may comprise PVC. The doped first polymer may comprise PVA and methylene blue at a concentration of greater than 10% (w/v). Coating the substrate may include coating the substrate with the doped first polymer with a coat between 10-1000 micron thick. The application of a second polymer may include applying PLA at a thickness between 10-1000 micron.

The dye containing layer may be formed in several ways, using a crystalline dye, inclusion of dye in a hydrogel or doped into a soluble polymer. The first method may require the device to be dipped into a bath of a high concentration solution of solvate dye, the device may then be removed and dried to allow the dye to crystallize across the surface before the second polymer is applied. The second method may require the device to first be coated with a hydrogel containing a high dye concentration. It is known in the art that controlled diffusion of bioactive dyes from hydrogel media may be achieved using a guanosine and 8-bromoguanosine hydrogel.

A method of providing the dye may include applying it as a doped soluble polymer such that as the first layer is degraded and the second layer is able to dissolve into the blood. PVA is one material that may be suited to this application, it is water soluble, able to be doped and has a high level of demonstrated biocompatibility. As the surface coating becomes permeable, the polymer and the dye dissolve into the blood.

In view of this disclosure, it will be seen that technologies are generally described for a method and a device for detecting device colonization. Disclosed herein is an indwelling medical device configured to detect a biofilm. The device comprises a substrate configured to contact blood and a detecting material, disposed with the substrate, configured to detect the presence of a biofilm thereon. The detecting material is soluble in blood, removable by kidneys from the blood, and passable to urine by the kidneys for detection in the urine. A method for detecting the growth of a biofilm on an indwelling medical and a method for making an indwelling medical device are also disclosed herein.

Aspects of the indwelling medical device of the present disclosure comprise a substrate configured to be in contact with the blood which may be prone to biofilm colonization. Biofilm colonization may lead to sepsis increasing hospital stays, reliance on antibiotics and even fatalities. To mitigate or prevent this, removal of medical devices in early stage colonization may allow the risk of infection to be greatly reduced. The indwelling medical device of the present disclosure may provide an indication of biofilm growth thereon, suggesting device removal.

Aspects of the presently disclosed indwelling medical device may comprise a substrate or coating for that releases a dye into the blood when colonized by bacteria. For example, a two-layer dip coating may be provided. In this aspect, as the top layer is degraded by the biofilm it becomes porous allowing the detecting material or dye to diffuse from the lower layer out into the blood. The dye is then removed from the blood and passed through urine, presence of dye in urine may indicate the colonization of the device.

Aspects of the presently disclosed indwelling medical device may be applicable to a number of devices including intravenous catheters, central and arterial lines and wound drains. To determine which device is colonized, each device category may use a different colored dye, depending on the color of the dye output the device that is contaminated may be determined and replaced.

In at least one aspect of the present disclosure, an indwelling medical device comprises a dye-containing layer and a coating layer placed on the surface of the dye-containing layer. The device may be activated with colonization of the device which may lead to degradation of the coating layer, allowing dye from the dye containing layer to diffuse into the blood. The dye may then be removed from the blood by the kidneys and passed in the urine. Color change of urine may indicate colonization has occurred and dye color may indicate the affected device(s) or surface(s) thereof.

Aspects of the presently disclosed indwelling medical device may offer a simple, low cost surface coating for existing devices exposed to the blood. In the presence of a biofilm formation on the surface, the top layer may be degraded, exposing the underlying layer and releasing dye into the blood. The dye may be selected such that it is readily passed through urine, thus a change in urine color may be indicative of biofilm formation on device surface.

Aspects of the presently disclosed indwelling medical device may rely on the corrosive properties of the biofilm itself, degrading the surface coating through attachment and allowing the dye diffusion from the underlying layer, disposed on a substrate, into the blood. The surface coating may be sensitive to degradation and formed of a biocompatible material that has a degradation rate increase in response to the presence of a biofilm.

Aspects of the presently disclosed indwelling medical device may comprise a two-layer coating, the first layer may contain a dye that is readily dissolved into blood, filtered by the kidneys and passed through the urine. Several such dyes which may be suitable for this application including: methylene blue, β-carotene, rifampin, indocyanine green and betanin. Other dyes and detecting materials that are suitable as disposal through the urine may be incorporated with the presently disclosed indwelling medical device.

Other factors may be included with the dye to provide antimicrobial or antifouling factors. This includes, but is not limited to, direct antimicrobial compounds, e.g. methylene blue, silver ions, antibiotics or active enzymes to degrade the biofilm exopolymer matrix.

The dye or other detecting material may be contained in a layer from which it may directly and rapidly be released into the blood. The dye may be incorporated such that as the surface coating is corroded by the microbes, the dye is able to dissolve into the blood stream either by direct contact or diffusion through the surface layer. The dye containing layer may be formed in several ways, using a crystalline dye, inclusion of dye in a hydrogel or doped into a soluble polymer. The first method may require the device to dipped into a bath of a high concentration solution of solvate dye, the device may then removed and dried to allow the dye to crystallize across the surface before the second polymer is applied. The second method may require the device to first be coated with a hydrogel containing a high dye concentration. Controlled diffusion of bioactive dyes from hydrogel media may be realized using a guanosine and 8-bromoguanosine hydrogel. A further method of providing the dye is to apply it as a doped soluble polymer such that as the first layer is degraded the second layer is able to dissolve into the blood. Polyvinyl alcohol is one material suited to this application, it is water soluble, able to be doped and has a high level of demonstrated biocompatibility. As the surface coating becomes permeable the polymer and the dye dissolves into the blood.

Surface coating materials may be formed of one of a number of candidates broadly divided into three categories: polymer coating, mixed polymer coating or metallic coating. For example, single polymer coating methods offer one possible method of providing a surface coating, a number of materials may be suitable, a benefit may be the simple processing requirements. A number of biodegradable polymers may be suitable for this application including starch-based polymers, cellulose-based polymers, PLA and PLG. Polymer coatings may provide and auxiliary benefit of gradual degradation occurring within the body over time allowing the coating to be used as an indicator of time in place in the absence of colonization, allowing the device to provide information of biofouling contamination as well as monitoring time in the body.

Polylactic acid (PLA) may provide an effective material for biomedical applications, due to its high biocompatibility, controllable degradation rates, and simple processing, and may make it advantageous for use in the presently disclosed indwelling medical device. Degradation characteristics of PLA may provide additional benefits as degradation may be mediated both by enzymatic degradation and microbial degradation which may allow the material to be readily degraded both during early and late biofilm formation. Additionally, PLA may be preferred due to low cost, simple processing, relatively low melting point (180° C.) and widespread clinical application. Due to these properties PLA may be readily applied as a dip coating to the device whilst retaining desired mechanical properties. Use of PLA-co-PLG (PLGA) in place of pure PLA in the presently disclosed indwelling medical device may provide for improved control of degradation rates based on relative proportion of the two monomers.

Alternatively the top coating layer may be constructed from protein, e.g. albumin. Biofilms are known to secrete large amounts of protease enzymes throughout development. These enzymes are mostly localized within the biofilm causing erosion of the protein layer. Over time this may lead to dye release. A top coating, or layer disposed to be in direct contact with blood, may comprise albumin coated microbubbles which may also provide desired characteristics. The capability to maintain a gas core within an albumin shell may indicate that the coating provides the low permeability that may be desired.

In at least one aspect of the present disclosure, an indwelling medical device, mixes of polymers may be used, as opposed to utilizing pure polymers. For example, one polymer being degraded in the presence of the biofilm and the second providing structure such that as the first polymer is degraded the overall structure becomes permeable rather than eroding completely. In this case, a readily degraded polymer is mixed with a structurally supportive polymer. An advantage of this aspect may be that it may provide a surface for the biofilm to remain attached to, thus preventing release of the biofilm during device removal.

A number of structural polymers such as silicone rubber, polyurethane and polyethylene may provide a retaining structure for biofilm. During processing, the polymer may be mixed with a degradable polymer or protein such as those previously disclosed. In the presence of a biofilm the surface may be partially degraded, allowing blood to diffuse into the dye containing layer or portion of the indwelling medical device and solvate the dye. The structural polymer may remain unaffected by the presence of the biofilm, providing a structure for which the film can remain adhered to, preventing or mitigating any excessive release of free microbes during the device response and removal.

Alternatively, metallic coating layers may offer another method of providing controlled biofilm induced degradation, in part, this may be facilitated by microbially induced corrosion. For example, rather than providing a polymer coating, a thin film of iron or magnesium may used due to biocompatibility and the use of these metals in resorbable implantable stents. A thin coating of the metallic surface may be applied (preferably <500 um) which may be achieved in a number of ways: chemical vapor deposition, evaporation deposition or electroplating.

In at least one aspect of the present disclosure, an indwelling medical device comprises at least one material suitable for use as a surface coating for devices in contact with blood. This encompasses a large number of frequently used devices, used in both long and short-term treatments. Applicable devices include: cannulae, both intravenous and arterial, central lines and dialysis catheters. Additionally the technology may be applied to wound drains. Biofilm detection technology currently may be limited to complex systems, and the presently disclosed indwelling medical device may provide a simple, low cost and/or effective marker suitable for application to a number of devices. Advantages of the presently disclosed indwelling medical device may include, obvious signal providing indication of device colonization, allowing multiple devices in place simultaneously to provide separate signals, may not require changes from current practice, may be made of low cost of materials with FDA approved materials available, and/or may be applicable to a range of devices.

In recent years, absorbable metallic medical device structures have been of significant interest for stent construction due to enhanced mechanical properties compared to polymers. This supports the aspect of the present disclosure of utilizing metallic coatings as a biofouling responsive surface. It is known that a medical device comprising metals may be configured for biocorrosion to occur within the body wherein the macroscopic metallic structures may be safely absorbed.

In at least one aspect of the present disclosure, an indwelling medical device comprises methylene blue. Methylene blue is widely used as a dye and drug with a range of properties. Oral and intravenous administrations have been shown to be safe, with daily doses of 1-2 mg/kg administered 2-3 times per day (100-300 mg in total) used to treat methemoglobinemia, for example. These concentrations have been demonstrated to be safe for short treatment duration. Due to the small quantity of methylene blue used in the indwelling medical device of the present disclosure, and the rapid rate of filtration from blood, toxicity risks may be low.

Degradation kinetics of PLA in the presence of a biofilm may not be fully known, however significant research regarding degradation due to a number of microbial species has been well established. As is known in the art, a mechanism was identified as enzymatic degradation, mediated by a number of proteases, esterases and lipases. Additionally low pH is known to accelerate the hydrolysis of PLA and poly(lactic-co-glycolic acid) (PLGA), as is using low porosity polymer material as may be utilized in the indwelling medical device of the present disclosure.

Aspects of the indwelling medical device of the present disclosure may comprise a surface coating suitable for contact with blood. A large number of frequently used indwelling medical devices, used in both long and short-term treatments, are within the scope of the present disclosure. For example, aspects of the indwelling medical device of the present disclosure may comprise cannulae, both intravenous and arterial, central lines, dialysis catheters, peripherally inserted central catheter (PICC line). Additionally, one or more aspects of the indwelling medical device of the present disclosure may be applied to wound drains.

Aspects of the indwelling medical device of the present disclosure may provide one or more features such as: obvious signal providing indication of device colonization; a system comprising multiple indwelling medical devices in place simultaneously, each providing separate signals; indwelling medical device which may not require changes from current medical practice; indwelling medical device which may have relatively low cost of materials with FDA approved materials available; a signaling or detecting material or system which may be applicable to a range of indwelling medical devices.

Current Biofilm detection technology may be limited to complex and/or costly systems. Aspects of the indwelling medical device of the present disclosure may offer a simpler, lower cost, and/or an effective marker suitable for application to a number of indwelling medical devices. The function of the presently disclosed indwelling medical device may be based on established methods and/or using clinically approved materials.

In recent years, absorbable metallic medical device structures have been of significant interest for stent construction due to enhanced mechanical properties compared to polymers. Aspects of the present disclosure may offer support to the concept of utilizing metallic coatings as a biofouling responsive surface. For instance, biocorrosion may occur within the body and macroscopic metallic structures may be safely absorbed without negative health consequence, which may enable one or more aspects of the present disclosure to detect the presence of a biofilm on an indwelling medical device.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application.

The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An indwelling medical device configured to detect a biofilm, the device comprising:
   a substrate configured to contact blood;
   a detecting material, disposed in or about the substrate, configured to detect the presence of a biofilm on the indwelling medical device;
   the detecting material being soluble in blood, removable by kidneys from the blood, and passable to urine by the kidneys; and
   the indwelling medical device being configured to solubilize a sufficient amount of the detecting material, upon a sufficient presence of the biofilm on the indwelling medical device, for detection in the urine to indicate the presence of the biofilm on the indwelling medical device.

2. The indwelling medical device of claim 1 wherein the detecting material is selected from the group consisting of methylene blue, β-carotene, rifampin, Yellow No. 6, tetracycline, Red No. 40, Red No. 3, Blue No. 2, Evan's Blue, Green No. 3, Blue No. 1, indocyanine green, and betanin.

3. The indwelling medical device of claim 1 further comprising a first layer disposed on the substrate.

4. The indwelling medical device of claim 3 further comprising:
   a second layer disposed on the first layer, the second layer being degradable in the presence of the sufficient amount of biofilm for the release of the detecting material into the blood.

5. The indwelling medical device of claim 1 wherein the detecting material is visually detectable in the urine.

6. The indwelling medical device of claim 4 wherein the second layer comprises a polymer, mixed polymer, or metal.

7. The indwelling medical device of claim 4 wherein the second layer comprises a biodegradable material.

8. The indwelling medical device of claim 4 wherein the second layer comprises a material selected from the group consisting of starch-based polymers, cellulose-based polymers, PLA, PLG, and PLGA.

9. The indwelling medical device of claim 4 wherein the second layer comprises a protein or albumin.

10. The indwelling medical device of claim 4 wherein the second layer comprises a first polymer and a second polymer;
    the first polymer being degraded in the presence of a biofilm; and
    the second polymer providing a retaining structure for the biofilm, upon the degradation of the first polymer.

11. The indwelling medical device of claim 10 wherein the second polymer is selected from the group consisting of silicone rubber, polyurethane, and polyethylene.

12. The indwelling medical device of claim 4 wherein the second layer comprises a thin film of iron or magnesium.

13. The indwelling medical device of claim 4 wherein the second layer comprises at least one antimicrobial or antifouling agent.

14. The indwelling medical device of claim 1 wherein the indwelling medical device is an intravenous catheter, central line, arterial line, stent, or wound drain.

15. A system comprising two or more of the indwelling medical devices of claim 1, each the indwelling device comprising a different detecting material, each of the different detecting materials being independently detectable.

16. A system configured to independently detect biofilm on two or more indwelling medical devices, each of the indwelling medical devices comprising:
 a substrate configured to contact blood; and
 a detecting material disposed in or about the substrate configured to detect the presence of a biofilm;
 the detecting material being soluble in blood, removable by kidneys from the blood, and passable to urine by the kidneys;
 wherein each of the two or more indwelling medical devices is associated with an independently detectable detecting material, detection of the independently detectable detecting material indicating the indwelling medical device having the biofilm; and
 each of the two or more indwelling medical devices being configured to solubilize a sufficient amount of its associated detecting material, upon a sufficient presence of the biofilm on the associated indwelling medical device, for detection in the urine to indicate the presence of the biofilm on the associated indwelling medical device.

17. A method for detecting the growth of a biofilm on an indwelling medical device comprising:
 passing blood over a surface of the indwelling medical device;
 degrading the surface of the indwelling medical device, with a biofilm, by an amount sufficient to release a detecting material therefrom;
 releasing a sufficient amount of the detecting material from the surface of the indwelling medical device into the blood to become detectable in urine; and
 detecting the detecting material in the urine.

18. The method of claim 17 wherein the step of degrading the surface of the indwelling medical device comprises degrading at least a portion of the outer surface, contacting the passing blood, of the indwelling medical device by a sufficient amount, prior to the step of releasing the detecting material from the surface of the medical device.

19. The method of claim 18 wherein the step of degrading the surface of the indwelling medical device further comprises exposing an inner layer of the indwelling medical device to the passing blood and the step of releasing a sufficient amount of the detecting material from the surface of the indwelling medical device comprises releasing the detecting material from the inner layer.

20. The method of claim 17 wherein the step of detecting the detecting material in the urine comprises visually detecting the detecting material.

21. A method for making an indwelling medical device comprising:
 providing a substrate for use as an indwelling device;
 applying a detecting material in or about the substrate of the indwelling medical device;
 wherein the detecting material is soluble in blood, removable by kidneys from the blood, and passable to urine by the kidneys; and
 the indwelling medical device being configured to solubilize a sufficient amount of the detecting material, upon a sufficient presence of a biofilm on the indwelling medical device, for detection in the urine to indicate the presence of the biofilm on the indwelling medical device.

22. The method for making an indwelling medical device of claim 21 further comprising:
 preparing a bath comprising a crystalline solvate dye;
 the step of applying a detecting material in or about the substrate comprises coating the substrate of the indwelling medical device with the bath;
 drying the substrate coating and crystallizing the dye; and
 applying a polymer onto the crystallized dye.

23. The method for making an indwelling medical device of claim 21 further comprising:
 preparing a hydrogel and dye material; and
 the step of applying a detecting material to the substrate comprises coating the substrate of the indwelling medical device with the hydrogel and dye material.

24. The method for making an indwelling medical device of claim 23 wherein the hydrogel is selected from the group consisting of guanosine and 8-bromoguanosine hydrogel.

25. The method for making an indwelling medical device of claim 23 wherein:
 the step of preparing a hydrogel and dye material comprises doping a first polymer with a dye;
 the first polymer is water soluble;
 the step of applying a detecting material to the substrate comprises coating a substrate of the indwelling medical device with the doped first polymer; and
 applying a second polymer onto the coated substrate, wherein the second polymer is degradable in the presence of a sufficient amount of biofilm for the release of a detectable amount of the dye into the blood.

26. The method for making an indwelling medical device of claim 25 wherein the first polymer is PVA.

27. The method for making an indwelling medical device of claim 26 wherein:
 the substrate of the indwelling medical device comprises PVC;
 the doped first polymer comprises PVA and methylene blue at a concentration of greater than 10% (w/v); and
 the step of coating a substrate comprises coating the substrate with the doped first polymer with a coat between 10-1000 micron thick.

28. The method for making an indwelling medical device of claim 26 wherein the step of applying a second polymer comprises applying PLA at a thickness between 10-1000 micron.

* * * * *